United States Patent
Bechwati et al.

(10) Patent No.: US 10,357,221 B2
(45) Date of Patent: Jul. 23, 2019

(54) ANATOMICAL IMAGING SYSTEM WITH IMPROVED DETECTOR CALIBRATION PROCESS

(71) Applicant: Samsung Electronics Co., Ltd., Gyeonggi-do (KR)

(72) Inventors: Ibrahim Bechwati, Waltham, MA (US); Eric Bailey, North Hampton, NH (US); Geethika Weliwitigoda, Danvers, MA (US)

(73) Assignee: Samsung Electronics Co., Ltd. (KR)

( * ) Notice: Subject to any disclaimer, the term of this patent is extended or adjusted under 35 U.S.C. 154(b) by 697 days.

(21) Appl. No.: 14/832,014

(22) Filed: Aug. 21, 2015

(65) Prior Publication Data

US 2016/0074002 A1   Mar. 17, 2016

Related U.S. Application Data

(60) Provisional application No. 62/040,483, filed on Aug. 22, 2014.

(51) Int. Cl.
*A61B 6/00* (2006.01)
*A61B 6/03* (2006.01)

(52) U.S. Cl.
CPC .............. *A61B 6/583* (2013.01); *A61B 6/032* (2013.01); *A61B 6/585* (2013.01)

(58) Field of Classification Search
CPC ......... A61B 6/032; A61B 6/583; A61B 6/582; A61B 6/585

See application file for complete search history.

(56) References Cited

U.S. PATENT DOCUMENTS

| | | | | |
|---|---|---|---|---|
| 4,352,020 A | * | 9/1982 | Horiba | A61B 6/583 250/252.1 |
| 4,962,514 A | * | 10/1990 | Hart | A61B 6/583 250/252.1 |
| 5,301,108 A | * | 4/1994 | Hsieh | A61B 6/032 378/8 |
| 5,615,279 A | * | 3/1997 | Yoshioka | G06T 11/005 378/7 |
| 5,651,046 A | * | 7/1997 | Floyd | A61B 6/583 378/207 |
| 5,774,519 A | * | 6/1998 | Lindstrom | A61B 6/032 378/18 |
| 5,867,553 A | * | 2/1999 | Gordon | A61B 6/032 378/146 |
| 6,040,580 A | * | 3/2000 | Watson | G01T 1/1611 250/363.03 |

(Continued)

*Primary Examiner* — David J Makiya
*Assistant Examiner* — Soorena Kefayati
(74) *Attorney, Agent, or Firm* — Pandiscio & Pandiscio

(57) ABSTRACT

A method for calibrating detectors in a CT scanner, wherein the new calibration process uses a combination of slab-based and water-based calibrations. By combining both calibrations, the complexity of each procedure can be reduced which will reduce restrictions on the quality of detectors used in the scanner. The slabs can be made out of commercially available material such as acrylic, and they will require no special treatment. Combining both calibrations also reduces the number of water phantoms needed for the calibration and the complexity of the calibration algorithm. Furthermore, the slabs can be shaped based on the scanner geometry so as to optimize the slab-based calibration step.

17 Claims, 25 Drawing Sheets

(56) References Cited

U.S. PATENT DOCUMENTS

| | | | | |
|---|---|---|---|---|
| 6,148,057 A * | 11/2000 | Urchuk | ............... | A61B 6/583 378/18 |
| 6,683,934 B1 * | 1/2004 | Zhao | ............... | A61B 6/032 378/37 |
| 6,848,827 B2 * | 2/2005 | Wu | ............... | A61B 6/583 378/19 |
| 6,944,258 B2 * | 9/2005 | Nukui | ............... | A61B 6/032 378/19 |
| 7,086,780 B2 * | 8/2006 | Wu | ............... | A61B 6/032 250/363.09 |
| 7,088,800 B2 | 8/2006 | Nukui et al. | | |
| 7,108,424 B2 * | 9/2006 | Heumann | ............... | G01D 3/022 250/252.1 |
| 7,134,787 B2 | 11/2006 | Sun et al. | | |
| 8,121,250 B2 * | 2/2012 | Dafni | ............... | A61B 6/032 378/18 |
| 8,315,352 B2 * | 11/2012 | Wu | ............... | A61B 6/032 378/18 |
| 8,611,625 B2 * | 12/2013 | Oohara | ............... | A61B 6/032 382/131 |
| 8,611,627 B2 * | 12/2013 | Wu | ............... | A61B 6/032 382/131 |
| 8,818,058 B2 * | 8/2014 | Paul | ............... | A61B 6/032 382/100 |
| 9,285,326 B2 * | 3/2016 | Gagnon | ............... | A61B 6/032 |
| 9,683,948 B2 * | 6/2017 | Gao | ............... | A61B 6/5258 |
| 2003/0058994 A1 * | 3/2003 | Sembritzki | ............... | A61B 6/06 378/108 |
| 2004/0196960 A1 * | 10/2004 | Tanigawa | ............... | A61B 6/032 378/207 |
| 2004/0228451 A1 * | 11/2004 | Wu | ............... | A61B 6/583 378/207 |
| 2005/0013414 A1 * | 1/2005 | Sun | ............... | A61B 6/4035 378/207 |
| 2006/0159223 A1 * | 7/2006 | Wu | ............... | A61B 6/032 378/18 |
| 2010/0027867 A1 * | 2/2010 | Bernhardt | ............... | A61B 6/00 382/132 |
| 2010/0195804 A1 * | 8/2010 | Dafni | ............... | A61B 6/032 378/207 |
| 2011/0293161 A1 * | 12/2011 | Yi | ............... | G06T 11/005 382/131 |
| 2012/0163557 A1 * | 6/2012 | Hsieh | ............... | A61B 6/032 378/207 |
| 2013/0026353 A1 * | 1/2013 | Yan | ............... | A61B 6/032 250/252.1 |
| 2013/0156163 A1 * | 6/2013 | Liu | ............... | A61B 6/482 378/207 |
| 2014/0072108 A1 * | 3/2014 | Rohler | ............... | A61B 6/482 378/207 |
| 2014/0321608 A1 * | 10/2014 | Ueki | ............... | A61B 6/032 378/18 |
| 2016/0157809 A1 * | 6/2016 | Takahashi | ............... | A61B 6/5258 378/16 |

* cited by examiner

THE TWO STEP OF THE COMBINED CALIBRATION PROCESS

SLAB BASED CALIBRATION STEPS

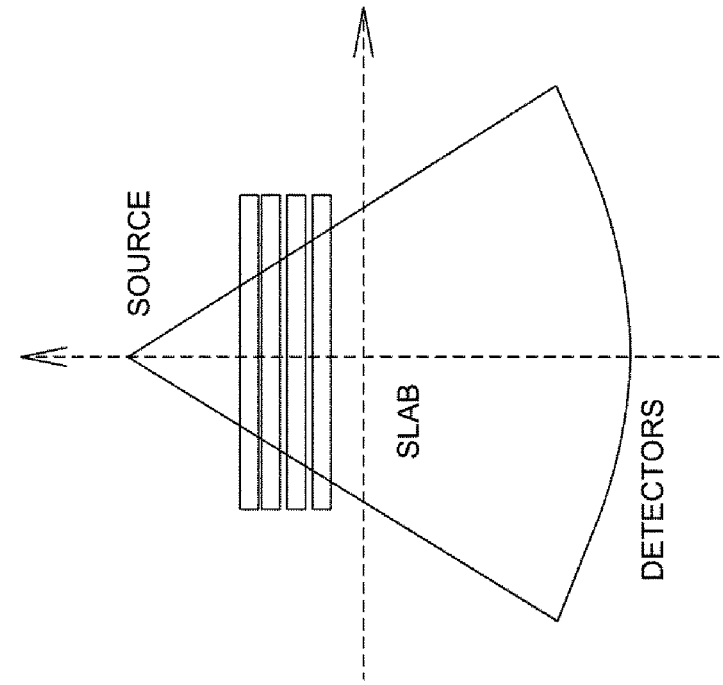
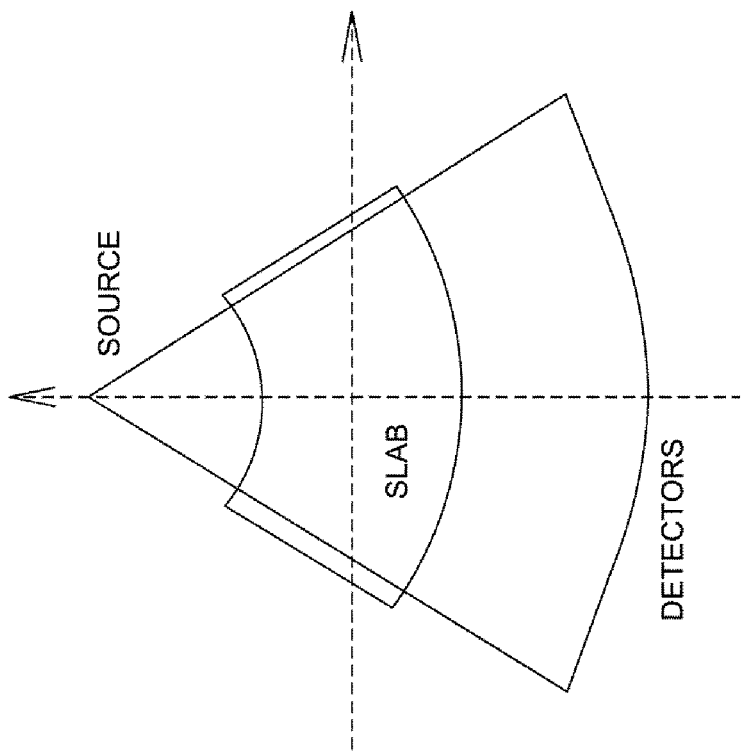
FIG. 9
THE SLAB POSITIONING IN THE X-RAY BEAM

THE DATA CORRECTION STEP

THE GENERATION OF SLAB COEFFICIENTS

INDIVIDUAL WATER PHANTOMS

INTERLOCKED WATER CYLINDERS

PLACEMENT OF A SMALL WATER PHANTOM IN THE SCANNER BORE

PLACEMENT OF A LARGE WATER PHANTOM IN THE SCANNER BORE

GENERATING THE IDEAL PROJECTION DATA

THE ADJUSTMENT OF SLAB-BASED COEFFICIENTS

ANATOMICAL IMAGING SYSTEM WITH IMPROVED DETECTOR CALIBRATION PROCESS

REFERENCE TO PENDING PRIOR PATENT APPLICATION

This patent application claims benefit of prior U.S. Provisional Patent Application Ser. No. 62/040,483, filed Aug. 22, 2014 by Neurologica Corp. and Ibrahim Bechwati et al. for ANATOMICAL IMAGING SYSTEM WITH IMPROVED DETECTOR CALIBRATION PROCESS, which patent application is hereby incorporated herein by reference.

FIELD OF THE INVENTION

This invention relates to imaging systems in general, and more particularly to anatomical imaging systems.

BACKGROUND OF THE INVENTION

In many situations it can be desirable to image the interior of opaque objects. By way of example but not limitation, in the medical field, it can be desirable to image the interior of a patient's body so as to allow viewing of internal structures without physically penetrating the skin.

Computerized Tomography (CT) has emerged as a key imaging modality in the medical field. CT imaging systems generally operate by directing X-rays into the body from a variety of positions, detecting the X-rays passing through the body, and then processing the detected X-rays so as to build a three-dimensional (3D) data set and a 3D computer model of the patient's anatomy. The 3D data set and 3D computer model can then be visualized so as to provide images (e.g., slice images, 3D computer images, etc.) of the patient's anatomy.

By way of example but not limitation, and looking now at FIGS. 1 and 2, there is shown an exemplary CT imaging system 5. CT imaging system 5 generally comprises a torus 10 which is supported by a base 15. A center opening 20 is formed in torus 10. Center opening 20 receives the patient anatomy which is to be scanned.

Looking next at FIG. 3, torus 10 generally comprises a fixed gantry 22, a rotating disc 23, an X-ray tube assembly 25 and an X-ray detector assembly 30. More particularly, fixed gantry 22 is disposed concentrically about center opening 20. Rotating disc 23 is rotatably mounted to fixed gantry 22. X-ray tube assembly 25 and X-ray detector assembly 30 are mounted to rotating disc 23 in diametrically-opposing relation, such that an X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disc 23 so that they are rotated concentrically about center opening 20, X-ray beam 40 will be passed through the patient's anatomy along a full range of radial positions, so as to enable CT imaging system 5 to create a "slice" image of the anatomy penetrated by the X-ray beam. Furthermore, by moving the patient and CT imaging system 5 relative to one another during scanning, a series of slice images can be acquired, and thereafter appropriately processed, so as to create a 3D data set of the scanned anatomy and a 3D computer model of the scanned anatomy. In practice, it is common to configure X-ray detector assembly 30 so that multiple slices of images (e.g., 8 slices, 16 slices, 32 slices, etc.) may be acquired with each rotation of rotating disc 23, whereby to speed up the acquisition of scan data.

In practice, it is now common to effect helical scanning of the patient's anatomy so as to generate a 3D data set of the scanned anatomy, which can then be processed to build a 3D computer model of the scanned anatomy. The 3D data set and 3D computer model can then be visualized so as to provide images (e.g., slice images, 3D computer images, etc.) of the patient's anatomy.

The various electronic hardware and software for controlling the operation of rotating disc 23, X-ray tube assembly 25 and X-ray detector assembly 30, as well as for processing the acquired scan data so as to generate the desired slice images, 3D data set and 3D computer model, may be of the sort well known in the art and may be located in torus 10 and/or base 15.

In many cases CT imaging system 5 is intended to be stationary, in which case base 15 of CT imaging system 5 is set in a fixed position on the floor of a room and a special motorized movable bed is provided to move the patient relative to CT imaging system 5 during scanning. More particularly, with a stationary CT imaging system 5, the patient is brought to the location of CT imaging system 5, the patient is placed on the motorized movable bed, and then the motorized movable bed is used to move the patient relative to CT imaging system 5 (i.e., to advance the patient into center opening 20 of CT imaging system 5) so that some or all of the length of the patient may be scanned by CT imaging system 5.

In other cases CT imaging system 5 is intended to be mobile so that the CT imaging system may be brought to the patient and the patient scanned at the patient's current location, rather than requiring that the patient be transported to the location of the CT imaging system. Scanning the patient with a mobile CT imaging system 5 can be highly advantageous, since it can reduce delays in patient scanning (e.g., the patient can be scanned in an emergency room rather than waiting to be transported to the radiology department) and/or it can allow the patient to be scanned without requiring movement of the patient (e.g., the patient can be scanned at their bedside in an intensive care unit, or "ICU"). To this end, and looking now at FIGS. 4 and 5, base 15 may comprise a transport assembly 50 for (i) moving mobile CT imaging system 5 to the patient prior to scanning and (ii) moving the CT imaging system relative to the patient during scanning. More particularly, transport assembly 50 preferably comprises (i) a gross movement mechanism 55 for moving CT imaging system 5 relatively quickly across room distances, so that the CT imaging system can be quickly and easily brought to the bedside of the patient, such that the patient can be scanned at their bedside without needing to be moved to the radiology department, and (ii) a fine movement mechanism 60 for moving the CT imaging system precisely, relative to the patient, during scanning so that the patient can be scanned on their bed or gurney without needing to be moved onto a special motorized movable bed. In one preferred form of the invention, gross movement mechanism 55 preferably comprises a plurality of free-rolling casters 62, and fine movement mechanism 60 preferably comprises a plurality of centipede belt drives 63 (which can be configured for either stepped or continuous motion, whereby to provide either stepped or continuous scanning of the patient). Hydraulic apparatus 65 permits either gross movement mechanism 55 or fine movement mechanism 60 to be engaged with the floor, whereby to facilitate appropriate movement of mobile CT imaging system 5. Thus, with a mobile CT imaging system 5, the CT mobile imaging system may be pre-positioned in an "out of the way" location (e.g., in an unused corner of an emergency room) and then, when a patient requires scanning, the patient may be quickly and easily scanned at their bedside, by simply moving the mobile CT imaging system to the patient's bedside on gross movement mechanism 55 (e.g., casters 62), and thereafter moving the mobile CT imaging system during scanning on fine movement mechanism 60 (e.g., centipede belt drives 63).

In current CT imaging systems, X-ray detector assembly 30 typically comprises solid state or ceramic detectors.

A CT scanner equipped with solid state or ceramic detectors needs to be calibrated for two separate effects. The first is the calibration of the "beam hardening" effect due to the polychromatic nature of the X-ray spectrum. The second calibration is to compensate for variations in the spectral response of the detector caused by impurities in the detectors. Typically, the calibration process involves scanning well known materials (such as plastic or water) and determining an adjustment factor for each detector which reflects proper calibration for that detector. Some existing methods use cylindrical water phantoms of several diameters coupled with very complex mathematical procedures. Other calibration methods use solid slabs of well known materials.

The advantage of the water calibration method is its ability to deal with a low grade material. However, a successful water-based calibration requires several water phantoms and a special calibration "seed" that needs to be generated manually and fine-tuned for each scanner. As such, water calibration is a lengthy procedure.

Slab-based calibration is faster and requires a less complex mathematical algorithm. But the success of the slab-based calibration depends on the quality of the detector array, i.e., the similarity or the closeness of the spectral responses of the various detectors. This typically requires a costly process of "culling" detectors which significantly vary from a "norm", which increases the cost of the detectors. Slab-based calibration also requires specially designed slabs that minimize the beam hardening effect through the material of the slab.

Thus there is a need for an improved detector calibration process.

SUMMARY OF THE INVENTION

These and other objects of the present invention are addressed by the provision and use of an improved detector calibration process.

In the new detector calibration process, calibration is effected using a combination of both slab-based and water-based calibrations. By using a combination of both slab-based and water-based calibrations, the complexity of each calibration process can be reduced, which reduces restrictions on the quality of the detectors used in the scanner. The slabs can be made out of commercially available material (e.g., acrylic), and the slabs require no special treatment. Combining both slab-based and water-based calibrations also reduces the number of water phantoms needed for the calibration process and reduces the complexity of the calibration algorithm. Furthermore, the slabs can be shaped based in accordance with the scanner geometry so as to optimize the slab-based step in the calibration process.

In one preferred form of the present invention, there is provided a method for calibrating detectors in a CT scanner, the method comprising:
generating an initial set of calibration tables using a slab-based calibration process; and
improving the initial set of calibration tables using a water-based calibration process.

In another preferred form of the present invention, there is provided a method for calibrating detectors in a CT scanner, the method comprising:
using a slab-based calibration step to generate slab-based correction coefficients; and
using the slab-based correction coefficients from the slab-based calibration step as the seed in a water-based calibration step.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 9 shows the positioning of the slabs in the X-ray fan beam;

DETAILED DESCRIPTION OF THE PREFERRED EMBODIMENTS

In accordance with the present invention, there is provided an improved detector calibration process.

The New Detector Calibration Process in General

The new detector calibration process of the present invention combines slab-based calibration and the water-based calibration to reduce the complexity of the calibration process. The slab-based calibration step is used first to automatically generate the initial calibration tables for the subsequent water-based calibration step. The calibration tables produced by the slab-based calibration step replaces the manually generated "seed" traditionally used in the water-based calibration step. The slab-based calibration tables are generated according to the scanner. The slab-based calibration tables improve the subsequent water-based calibration step and reduce the number of water phantoms needed for the water-based calibration step and reduce the complexity of the calibration algorithm.

The slab-based calibration step comprises acquiring data using a set of slab phantoms. The data is then processed to generate the corrected attenuation data of the slab phantoms. The corrected attenuation data is then averaged so as to create a measured profile of the slab phantoms. Using the knowledge-based information about the slab, an ideal profile is generated using a combination of linear fitting and data smoothing. The averaged measured profile is then compared to the ideal profile of the entire slab phantom for each detector. Later, a polynomial correction (e.g., a second order polynomial correction) is generated using the ideal profile and the measured slab data. The coefficients of the polynomial correction are then stored in calibration tables and used as the "seed" for the next calibration step (i.e., the water-based calibration step).

The water-based calibration step begins with the acquisition of the water data phantoms. The data of the water phantoms is acquired at different locations in the scan field of view. The acquired data is then post-processed to generate attenuation profiles. The attenuation data is corrected using the calibration tables generated by the previous slab-based calibration step. Using the scanned data, an ideal profile is generated using fan beam re-projection. For each detector, the ideal and measured data is gathered using acquired data from all acquired water phantoms. The data is then compared and, using a first order or a second order polynomial fit, the data is fitted and the second order coefficients (generated earlier by the slab-based calibration step) are adjusted using the coefficients generated by the water-based calibration step so as to produce the final calibration tables.

Figure 1:
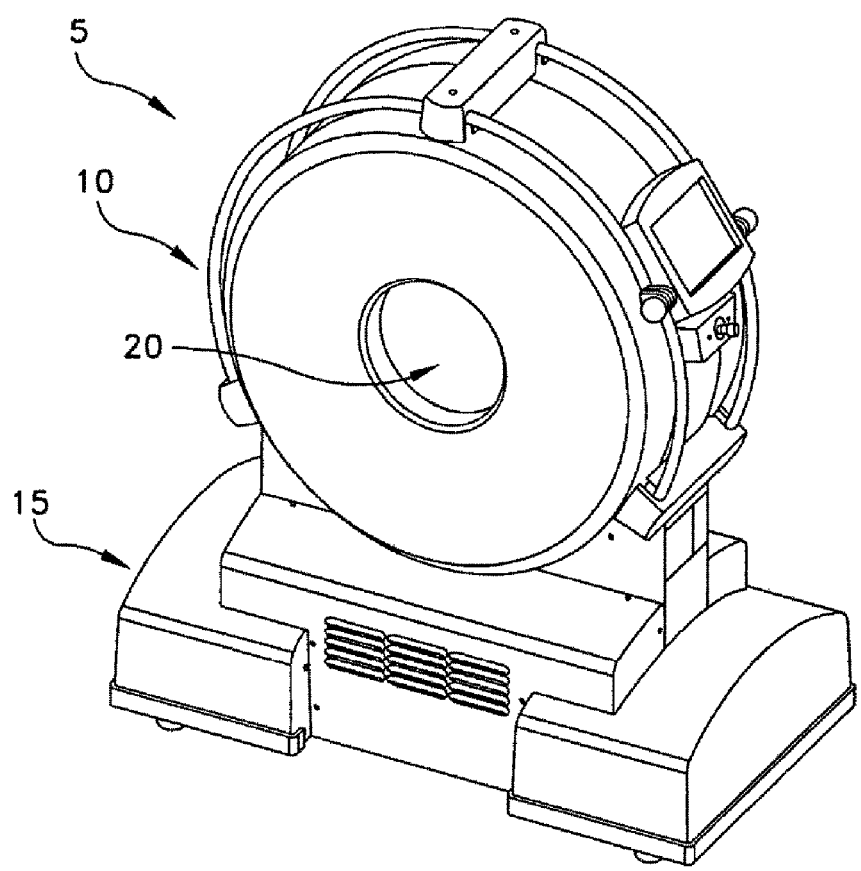
FIGS. 1 and 2 are schematic views showing the exterior of an exemplary CT imaging system.
Figure 2:
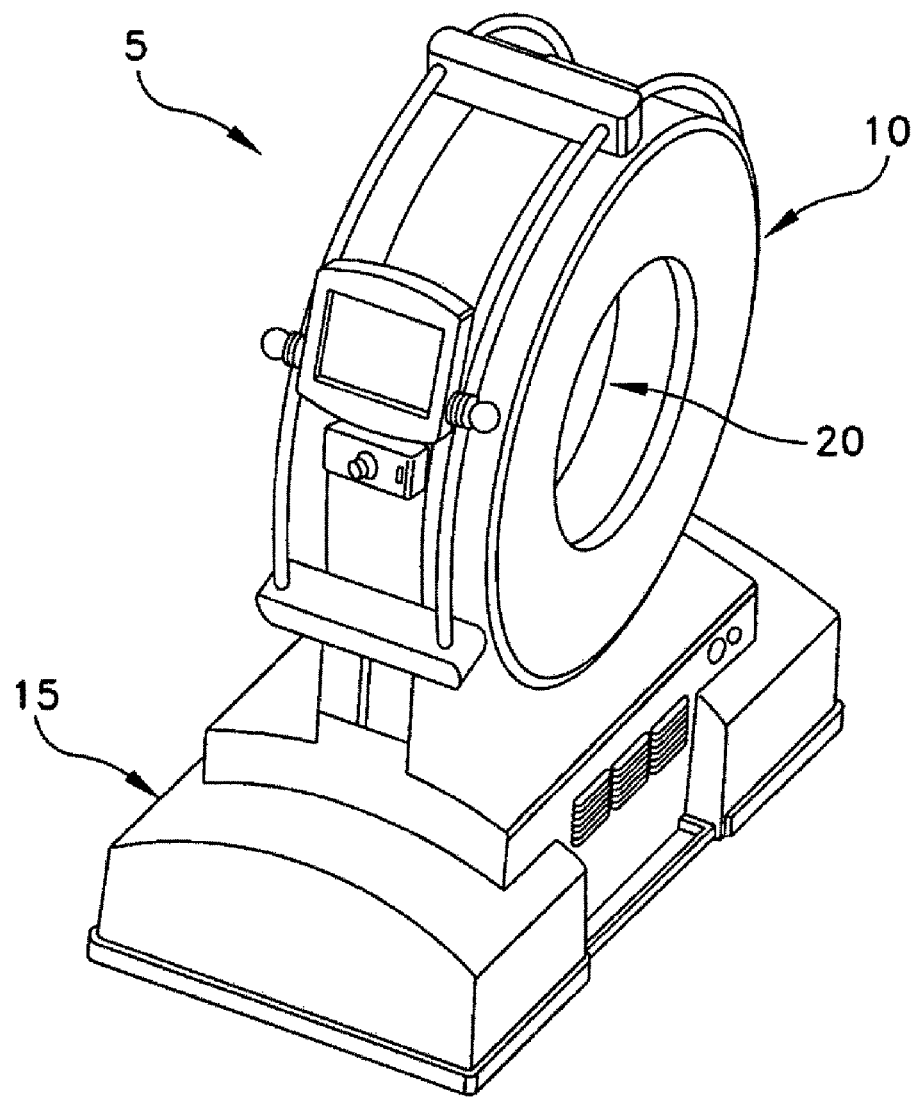
Figure 3:
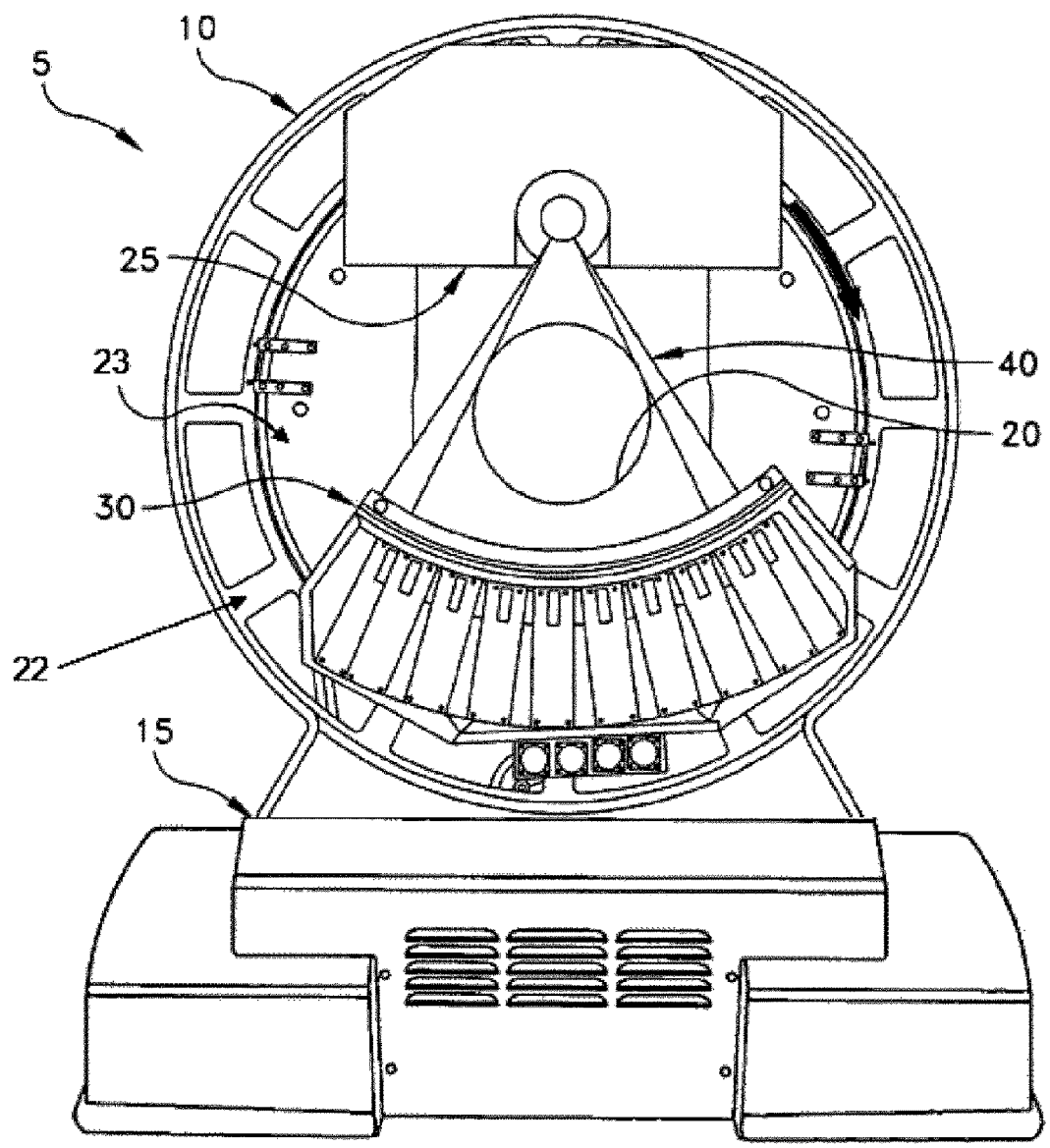
FIG. 3 is a schematic view showing various components in the torus of the exemplary CT imaging system shown in FIGS. 1 and 2.
Figure 4:
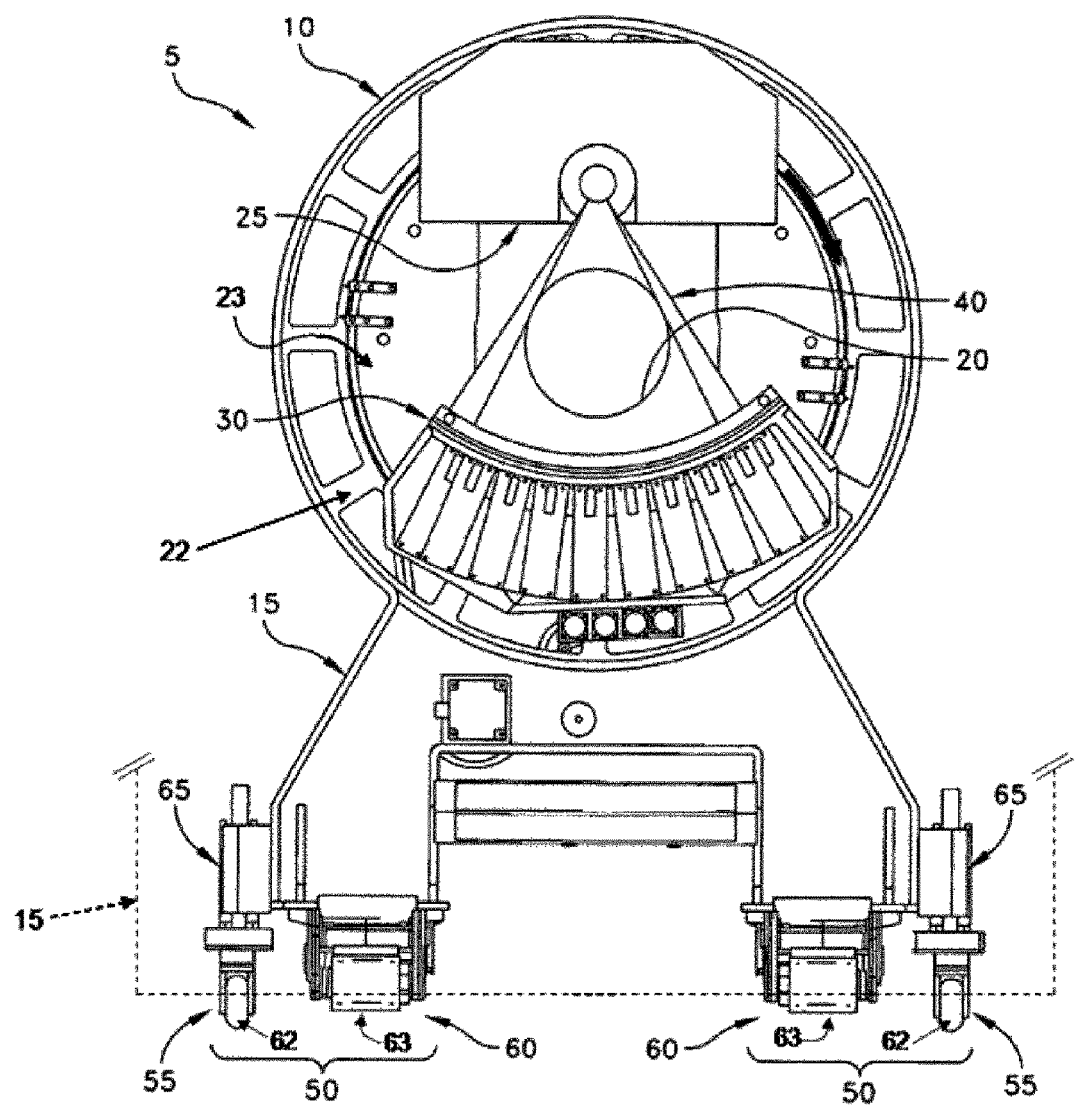
FIGS. 4 and 5 are schematic views showing an exemplary transport assembly for an exemplary CT imaging system.
Figure 5:
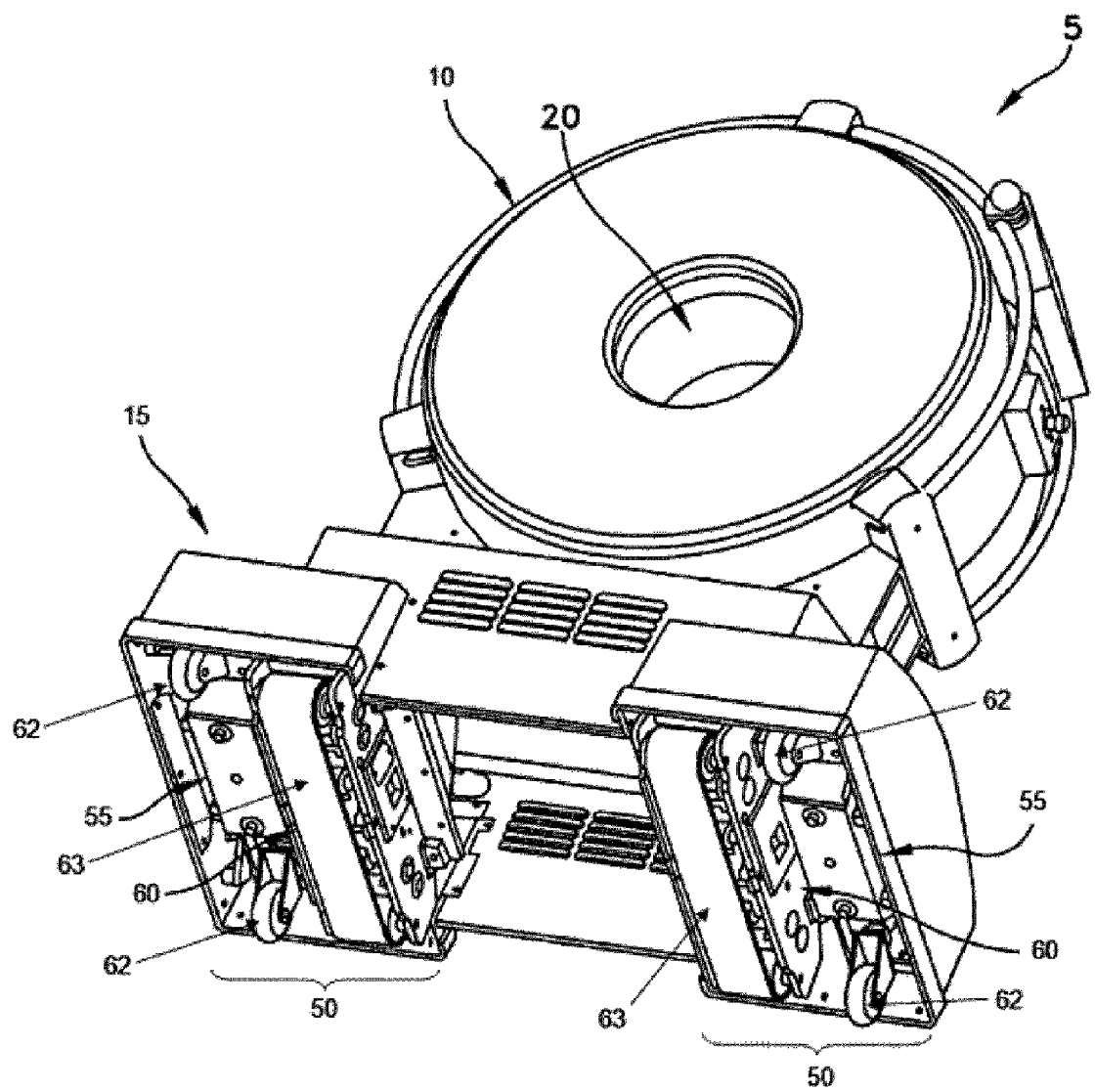
Figure 6:
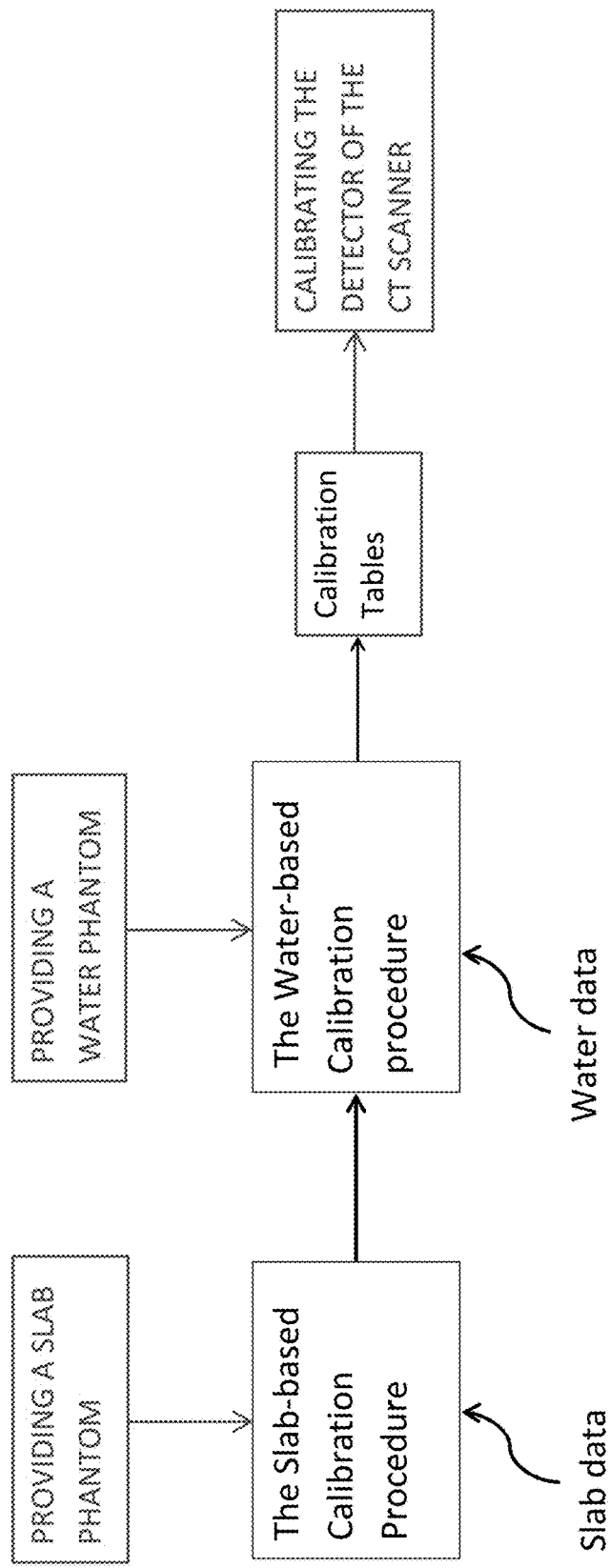
FIG. 6 is a schematic view of the non-linear calibration process of the present invention.

FIG. 6 is a schematic view of the non-linear calibration process of the present invention. The first step in the calibration process is the slab-based calibration step; the output of the slab-based calibration step is then used in the water-based calibration step for generating the final calibration tables (which are used to calibrate the detectors).

1. The Slab-Based Calibration Step

Figure 7:
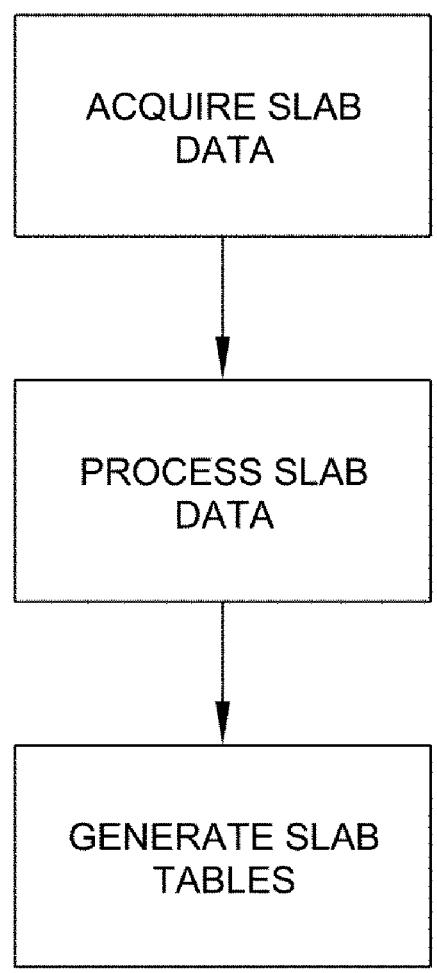
FIG. 7 shows the steps of the slab-based calibration process.

The slab-based calibration step comprises a data acquisition phase using specially designed slab phantoms. The acquired slab data is then processed to generate the slab tables. FIG. 7 shows the steps of the slab-based calibration process.

1.1 the Slab Phantoms

Figure 8:
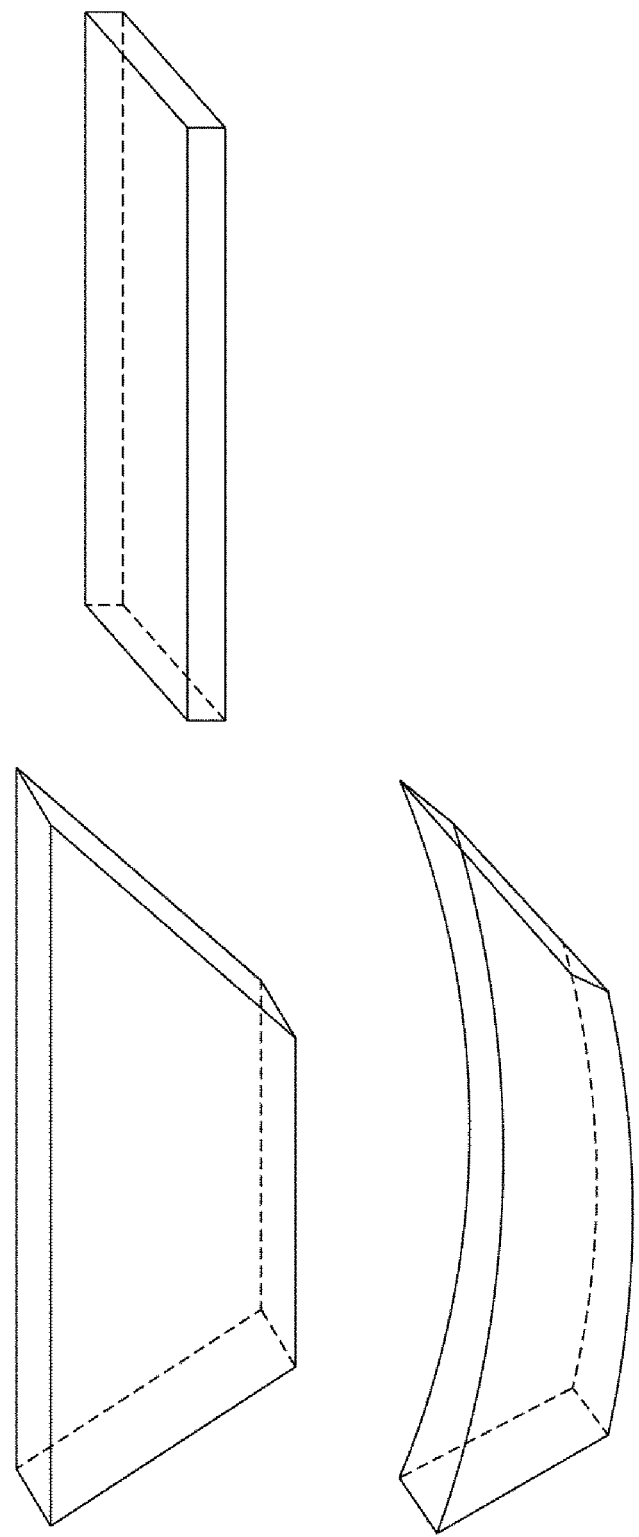
FIG. 8 shows the various types of slab phantoms.

The slab phantoms consist of multiple slabs made of the same material. It is preferable to choose a material that has similar properties to those of soft tissues, for example, the slabs can be made of "plastic water" (i.e., a plastic material chemically-altered to match the physical characteristics of water), acrylic, plastic or any other material. A thin piece of metal such as copper or aluminum can be taped to one side of the slab in order to "harden" the X-ray beam which passes through the slab. The slabs are typically made of rectangular pieces that can be stacked together. The slabs can be also be cut to match the scanner geometry, specifically, the scanner fan angles. Finally, the slabs can be shaped so as to generate the same path to each detector. FIG. 8 shows various exemplary slab phantoms.

1.2 the Positioning of the Slab Phantoms

The slabs can be placed in vertical or horizontal positions. The slabs can be positioned using a specially design slab holder that helps position the slabs. The slabs can also be positioned on top of the collimator, or on a patient table or in a phantom holder. The slabs have to be wide enough to cover the entire detector array, whether they are positioned vertically or horizontally. FIG. 9 shows the positioning of the slabs in the X-ray fan beam.

1.3 the Data Acquisition Step

The following data sets are acquired for each scan voltage and, optionally, for each collimation. It is important that the slab data be acquired without rotating the scanner gantry.

In a "first method", the slab raw data is acquired in what is known as "Service Mode". The data acquisition consists of the following steps:

1. Offset data: acquired in the absence of X-rays, the scan time should be at least as long as the time it takes for 3 rotations of the scanner gantry (when the scanner gantry is rotating).

2. Air data: acquired with the X-ray tube on, using low scan current in the absence of any object obstructing the X-ray beam. The scan should be at least as long as the time it takes for 3 rotations of the scanner gantry (when the scanner gantry is rotating).

3. The slab data: acquired with the X-ray tube on, the slab is positioned between the X-ray tube and the detector array. The scan current will be variable, dependent on the thickness of the slab.

In a "second method", the slab data acquisition is also done in Service Mode, however, the objective is to obtain attenuation data. The attenuation data can be acquired as follows:

1. Run the daily air calibration on the scanner.
2. Load a set of Null calibration tables.
3. Scan the slab in image mode without rotating the gantry.
4. The corrected slab data is then extracted from the scanner and used for the calibration.

Figure 10:
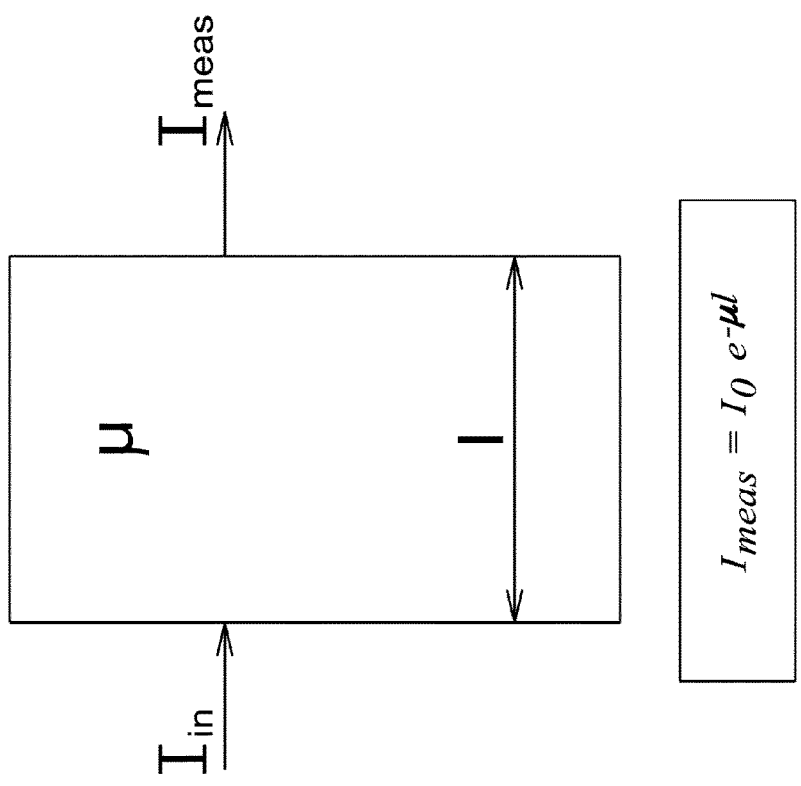
FIG. 10 shows the attenuation of an X-ray through a slab of width 1 and an attenuation μ.

In the aforementioned "first method" the acquired data is a function of the photon counts, $$I_{meas} = I_0 e^{-\mu l}$$

where $I_{meas}$ is the measured raw data, $I_0$ is the intensity of the X-ray beam from the source and $\mu l$ is the linear attenuation of the measured slab. FIG. 10 shows the attenuation of the X-ray through a slab of width l and an attenuation $\mu$.

The aforementioned "second method" measures the attenuation $\mu l$.

1.4 Slab Data Post Processing

The data post-processing step creates the attenuation data through the data correction process, using the raw data acquired in the first data acquisition method discussed in Section 1.3 above. The attenuation data is obtained as follows, for each acquired view:

1. Create an offset table using the offset data: O(d) is the calibrated offset of the $d_{th}$ detector.
2. Create an air table using the offset tables and the air data. A(d) is the calibrated gain of the $d_{th}$ detector.
3. Correct the raw slab data for offset: $S_o(d) = S_r(d) - O(d)$, where $S_o(d)$ is the offset corrected slab data of the $d_{th}$ detector, and $S_r(d)$ the acquired raw data of the $d_{th}$ detector.
4. Compute the log of the offset corrected data: $S_t(d) = \log(S_o(d))$.

5. Correct the logged data using the reference data:
$S_R(d)=s_l(d)-\log(\text{ref})$ 6. Correct the logged data using the air table. $S_a(d)=A(d)-S_R(d)$, $S_a(d)$ is the gain corrected logged data.

7. The attenuation of the slab is the gain corrected slab data: $\mu l(d)=S_a(d)$.

8. The slab attenuation data is also corrected for beam hardening.

Figure 11:
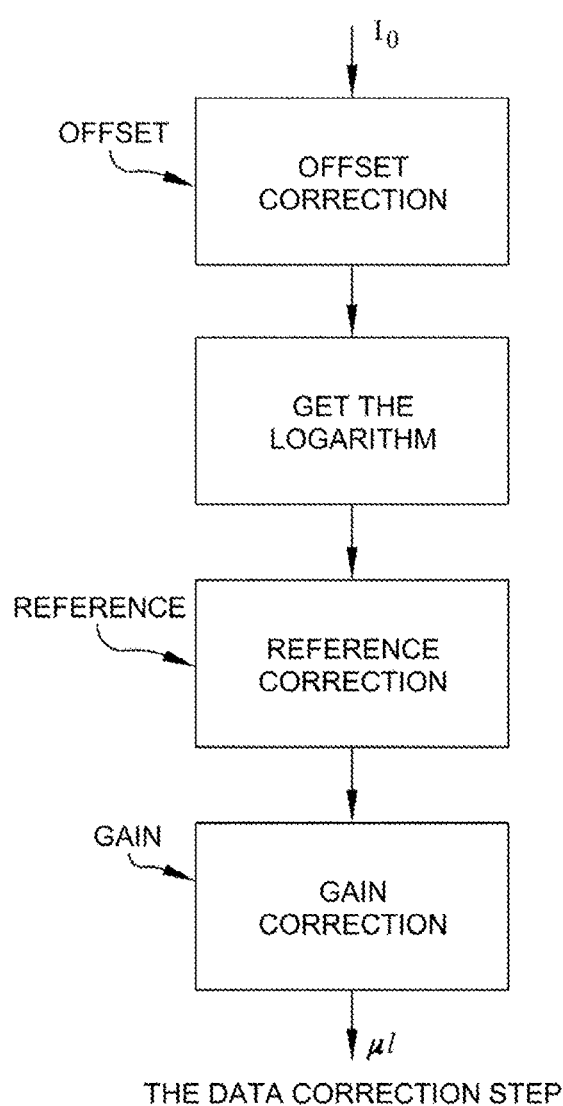
FIG. 11 shows the generation of the slab attenuation μl using the measured X-ray count.
Figure 12:
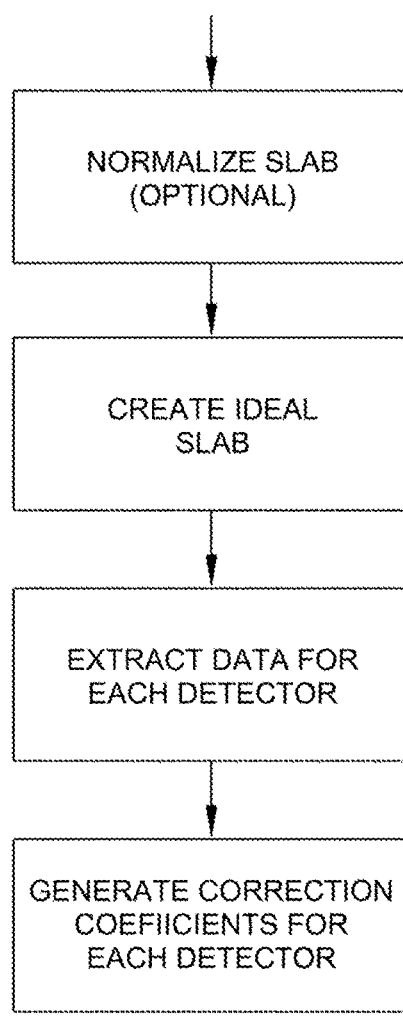
FIG. 12 shows the generation of slab coefficients.
Figure 13:
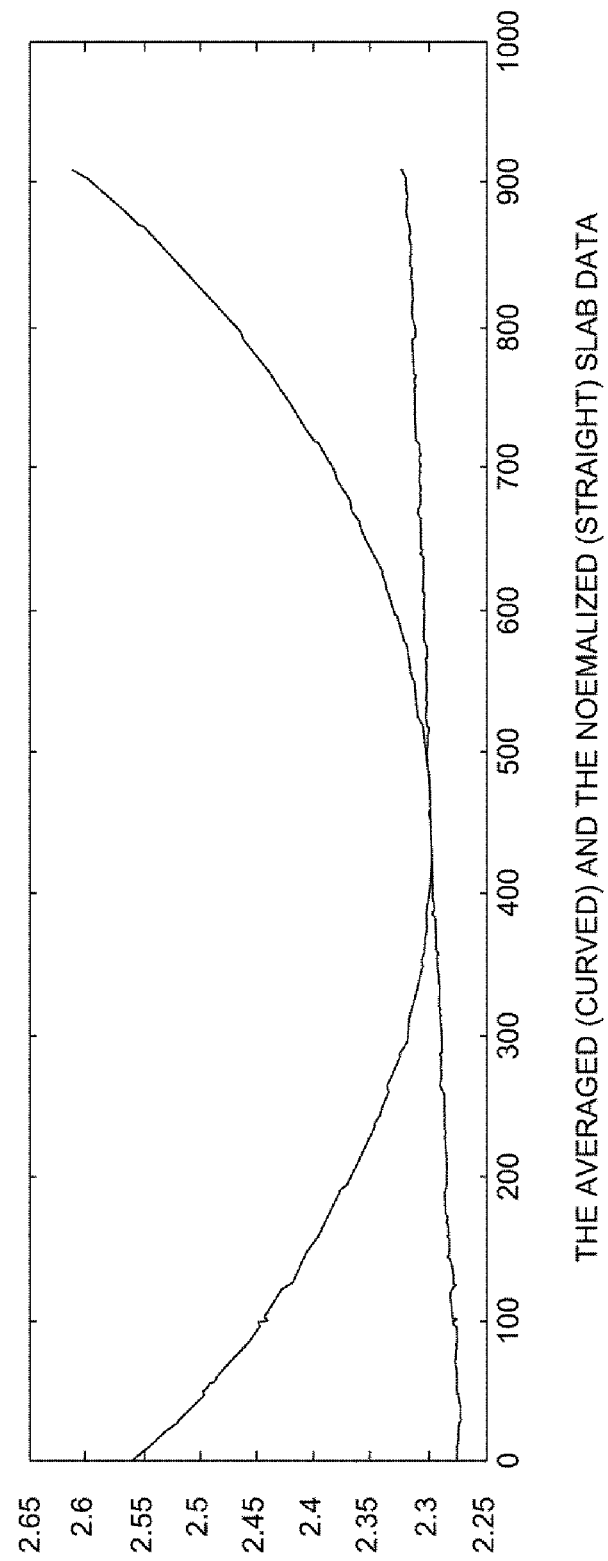
FIG. 13 shows the measured attenuation of the slab phantom.

FIG. 11 shows the generation of the slab attenuation μl using the measured X-ray count. FIG. 12 shows the generation of slab coefficients. FIG. 13 shows the measured attenuation of the slab phantom.

The aforementioned post processing step can be omitted if the data is acquired using the second acquisition method discussed in Section 1.3 above.

1.5 Generating the Slab Attenuation Profiles

The attenuation slab data is then processed to create an attenuation profile for each slab. The profile is obtained by averaging the corrected data over all the acquired views:

$$S^m(d) = \frac{1}{N_v} \sum_{i=0}^{N_v-1} \mu l_i^m(d)$$

where is the averaged attenuation data of the $d_{th}$ detector, $N_v$ is the number of acquired views, and $\mu l_i^m(d)$ is the corrected measured attenuation of the $i_{th}$ view and the $d_{th}$ detector. FIG. 13 shows the averaged attenuation profile of the slab. Based on the type of the slab phantom, the data may be normalized based on the X-ray path through the slab. The normalized attenuation is computed as follow:

$$S^n(d) = \frac{S^m(d)}{\cos(\gamma(d))}$$

where $\gamma(d)$ is the angle of the $d_{th}$ detector. FIG. 13 shows the averaged slab data (curved) and the normalized slab data (straight).

1.6 Generate the Ideal Slab Attenuation

An ideal profile of the slab is generated using either a linear fitting approach or a low-pass filter approach. The linear fitting approach is typically done using a Minimum Mean Square Estimate (MMSE):

$$\hat{S}^t(d) = \hat{a} S^n(d) + \hat{b} \text{ such as } \begin{cases} \hat{a} = \arg\max_a (S^n(d) - \hat{S}^t(d))^2 \\ \hat{b} = \arg\max_b (S_n(d) - \hat{S}^t(d))^2 \end{cases}$$

Figure 14:
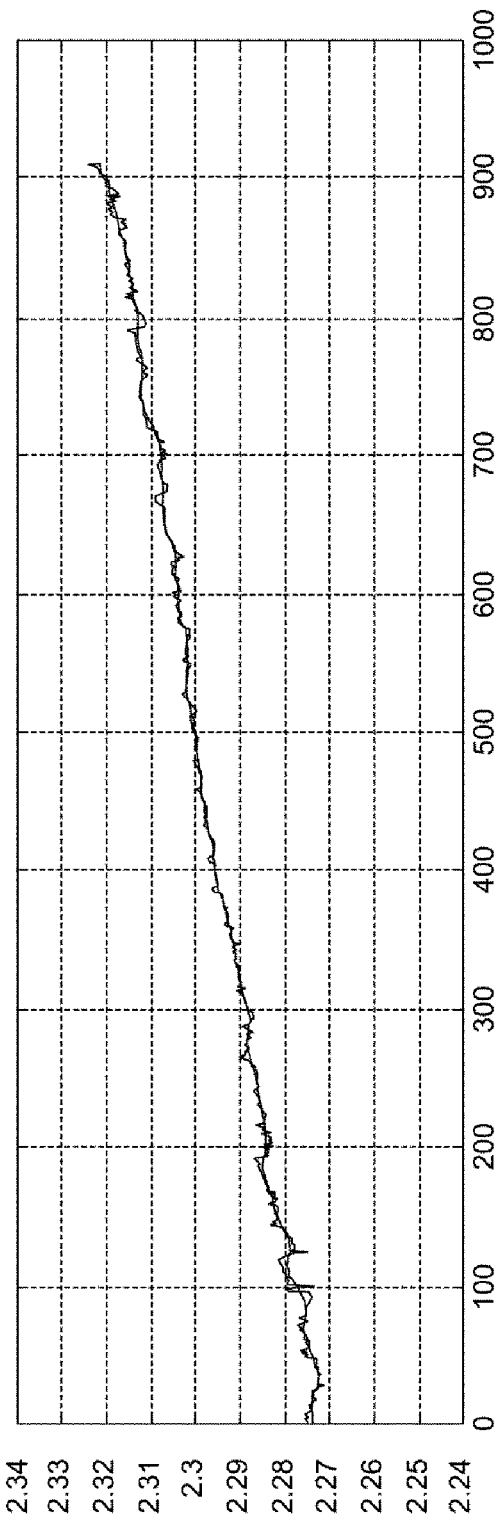
FIG. 14 shows the ideal and the measured slab data.

Using linear fitting, an ideal slab profile is computed using the MMSE method. The ideal slab profile can also be generated using a low-pass filter approach, the ideal profile is estimated as follow:

FIG. 14 shows the ideal and the measured slab data.

1.7 Extract the Measured and the Ideal Slab Data

The measured and the ideal slab data is extracted for each detector. For a given detector, the following two sets of data are extracted from both the measured and the estimated ideal data:

$$\begin{cases} \text{Measured data:} & S^{n,l}(d) \\ \text{Ideal data:} & S^{t,l}(d) \end{cases}$$

where l is the slab index; $l=0, \ldots, N_s$, and where $N_s$ is the number of slabs used in the calibration.

Figure 15:
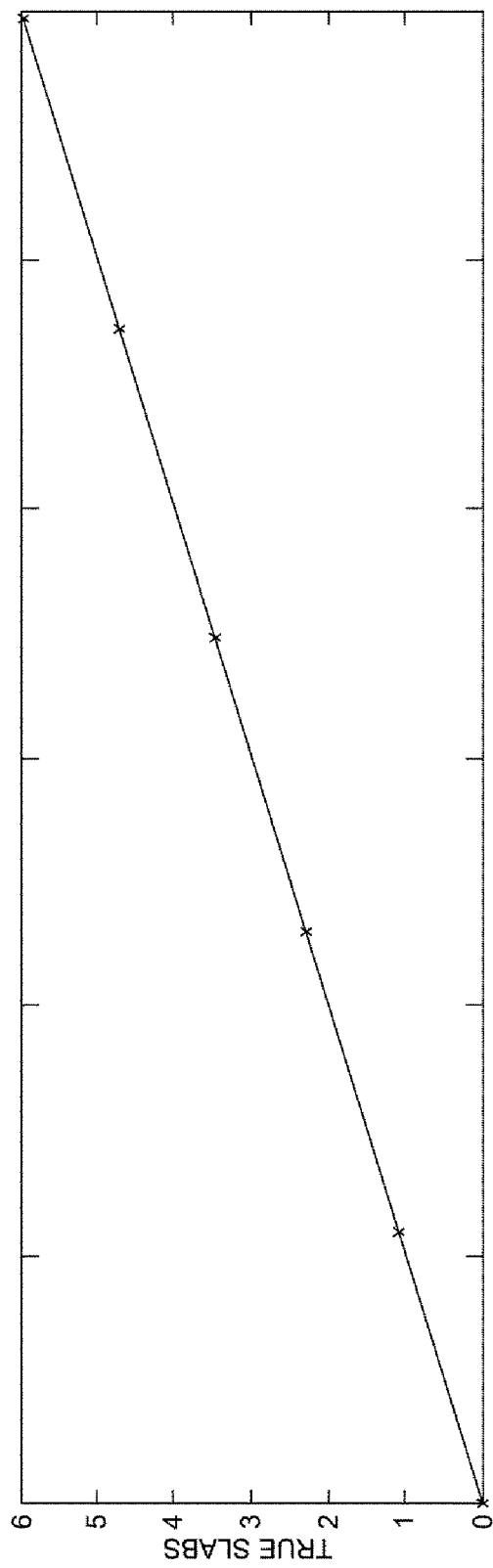
FIG. 15 shows the ideal versus the corrected or measured slab data.

FIG. 15 shows the ideal versus the corrected or measured slab data.

1.8 Compute the Slab-Based Calibration Correction Coefficients

The measured data of each detector is then "fitted" using a polynomial fit, and the correction coefficients are computed as the slab-based correction coefficients, $a_i$, are obtained using a second degree polynomial fit:

$$S^t(d) = \sum_{i=1}^{i=n} \alpha_i (S^n)^i$$

2. The Water-Based Calibration Step

The water-based calibration step can also be considered to be the slab-based coefficient adjustment step using the water phantoms. The water-based calibration step uses the data from the water phantoms to adjust the slab-based correction coefficients generated previously during the slab-based calibration step.

2.1 the Water Phantoms

Figure 16:
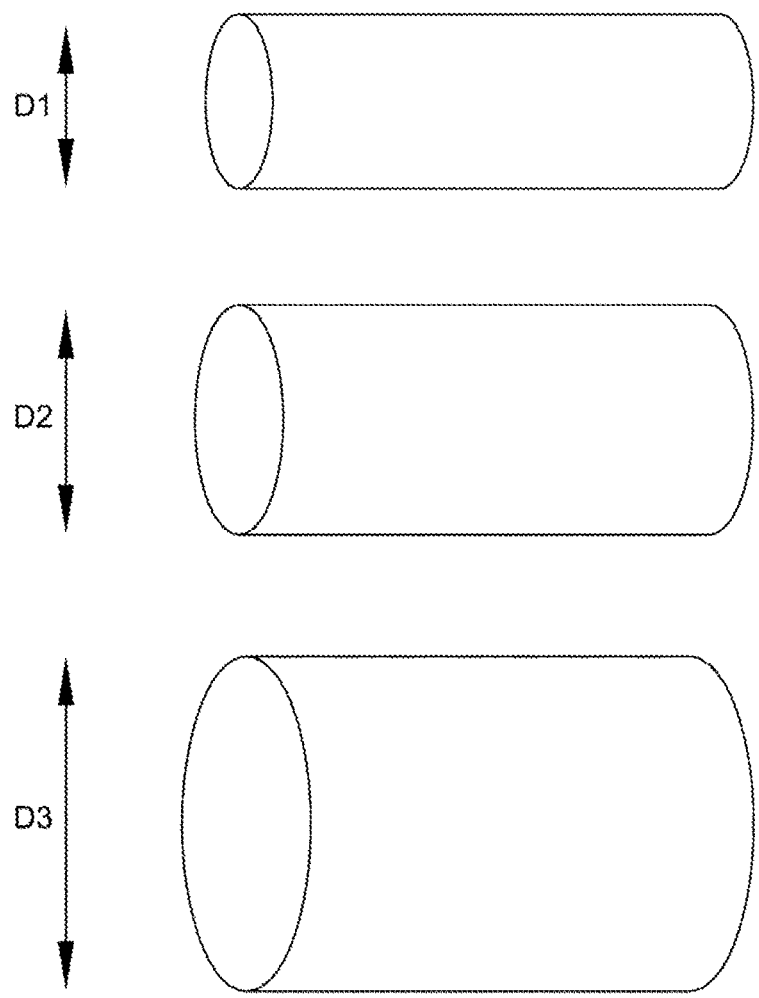
FIGS. 16 and 17 show individual cylinders and interlocked cylindrical water phantoms.
Figure 17:
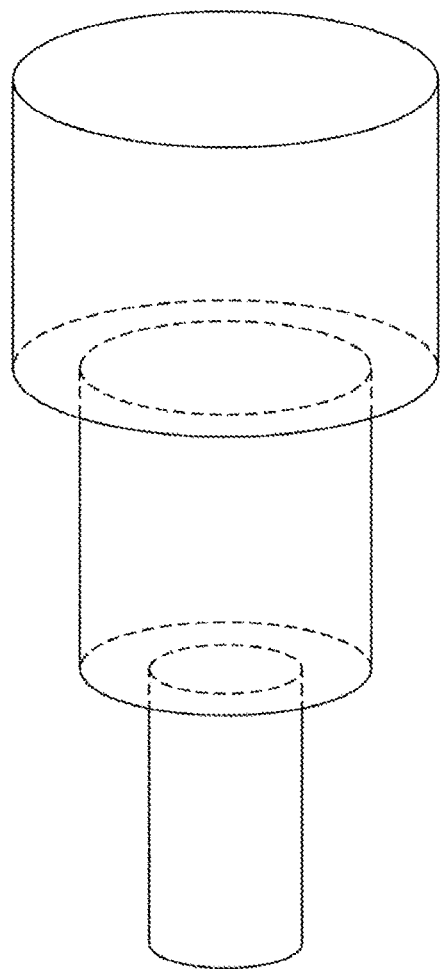

Water cylinders of several diameters can be used in the adjustment process. Ideally, the set of water phantoms should cover the attenuation range of a typical patient. The set of water phantoms consists of water cylinders with diameters ranging from 10 cm to 40 cm. The set can be made of individual cylinders or interlocked cylinders. FIG. 16 shows individual cylinders, and FIG. 17 shows interlocked cylindrical water phantoms. The water cylinder is typically made of acrylic.

2.2 the Positioning of the Water Phantoms

Figure 18:
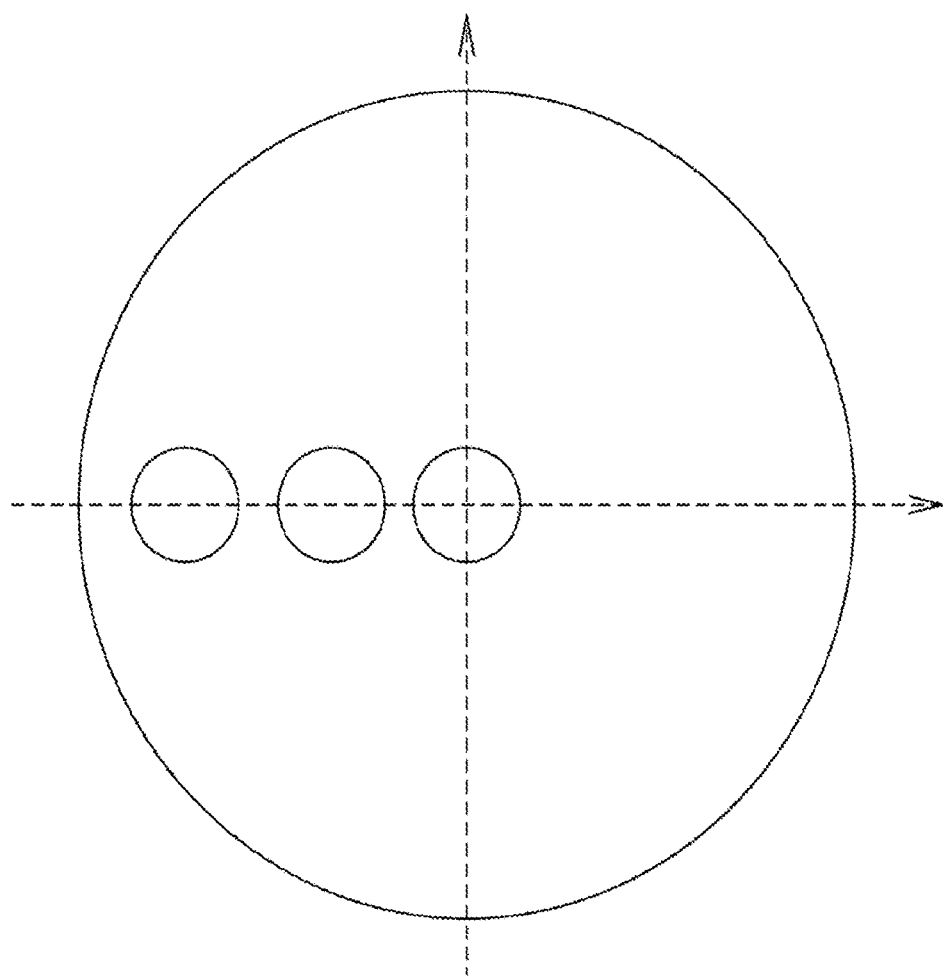
FIGS. 18 and 19 shows some possible placements of small and large water phantoms in the scanner field of view.
Figure 19:
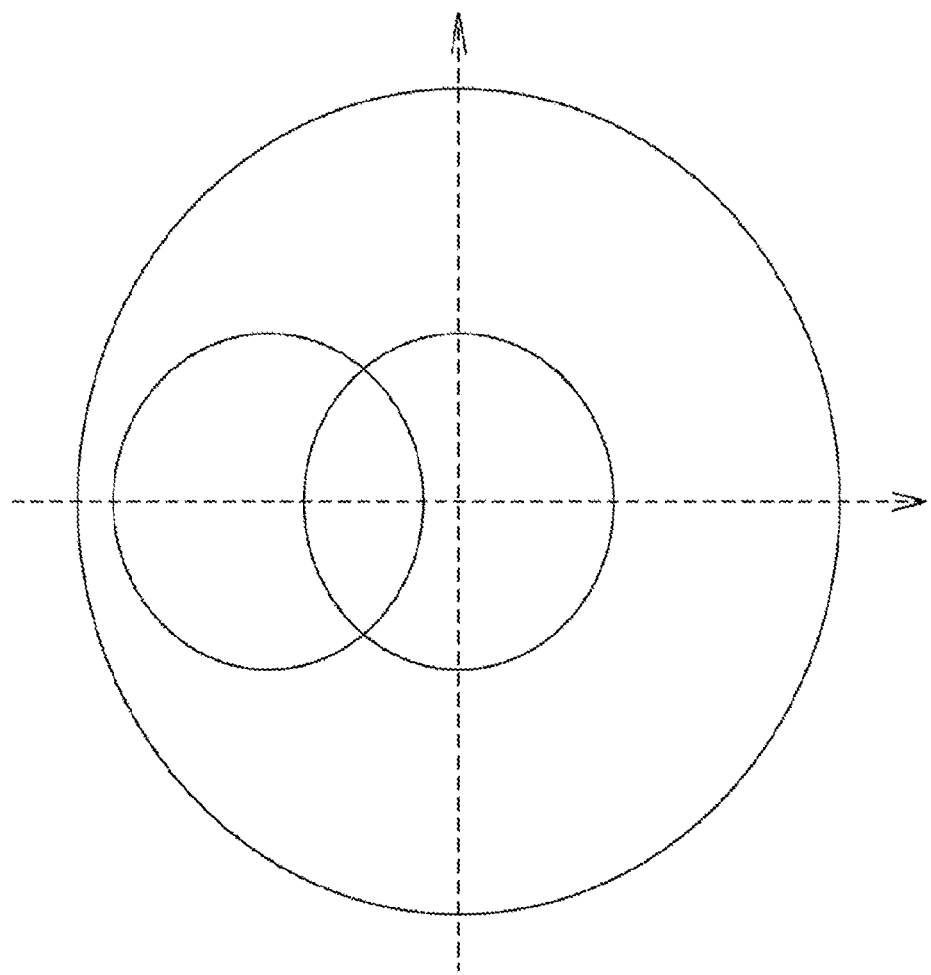

The water phantoms are positioned at different locations in the scan field of view based on their size. The main objective of positioning the water phantoms at different locations is to increase the detector coverage using different attenuation levels. Water phantoms with smaller diameters are placed at several locations in the scan field of view, typically, a centered position and two off-centered positions. Water phantoms with larger diameters may only need to be positioned twice in the field of view, a centered position and an off-centered position. Unlike other methods of detector calibration, where the water phantom positions are well defined and small tolerances are given for their placement, the new detector calibration process of the present invention does not require specific placement of the water phantoms. The water adjustment places no constraints on the positioning of the water phantoms in the scan field of views. FIGS. 18 and 19 shows some possible placements of small and large water phantoms in the scanner field of view.

2.3 The Data Acquisition

The water phantom data can be acquired in two different modes: "raw data acquisition mode", and "attenuation data correction mode". In both cases, the data is acquired in rotating mode, i.e., the gantry is rotating.

In the "raw data acquisition mode", only data is acquired and processing is accomplished using off-line computers:

1. Offset data: the data is acquired in the absence of X-rays; the data should be acquired over at least three rotations of the scanner gantry.

2. Air data: The data is acquired with the X-ray tube on, in the absence of any object in the scanner field of view. The scan current should be in the low 50's (mA) and the data should be acquired over at least three rotations of the scanner gantry.

3. Water phantom data: The data is acquired with the X-ray tube on; the water phantom is placed in the scanner field of view. The data should cover at least four rotations of the scanner gantry. The scan current depends on the size of the water phantom. A scan current in the scanner mid-range can be used for small water phantoms, e.g., phantoms with less than 20 cm diameter can be scanned using a 200 mA scan current. Larger water phantoms should be scanned at the upper-range of the scan current, e.g., a 200 to 300 mA scan current.

In the "attenuation data correction mode", the corrected data is extracted from the scanner and used in the adjustment of the initial slab-based correction coefficients:

1. Load the initial slab-based correction coefficient onto the scanner.
2. Set the acquisition parameters of a given scan, i.e., scan voltage, scan collimation, scan current and the scan time.
3. Complete the scan.
4. Review the scanned images.
5. Store the corrected data and the image data.

The scan time and the scan current can be adjusted for different scanners. The key objective is to collect enough statistical data to generate a reliable estimate of the differential gain error of the detectors.

2.4 The Data Post-Processing

Data post-processing will differ based on the data acquisition mode.

Where the data is acquired in the aforementioned "raw data acquisition mode" (see Section 2.3 above):

1. Create an offset table using the offset data: $O(d)$ is the calibrated offset of the $d_{th}$ detector.
2. Create an air table using the offset tables and the air data. $A(d)$ is the calibrated gain of the $d_{th}$ detector.
3. Correct the raw phantom data for offset: $W_o(d)=W_r(d)-O(d)$, where $W_o(d)$ is the offset corrected water data of the $d_{th}$ detector, and $W_r(d)$ is the acquired raw data of the $d_{th}$ detector.
4. Compute the log of the offset corrected data: $W_l(d)=\log(W_o(d))$.
5. Correct the logged data using the reference data: $W_R(d)=W_l(d)-\log(\text{ref})$.
6. Correct the logged reference corrected data using the air table. $W_a(d)=A(d)-W_R(d)$, where $W_a(d)$ is the gain corrected logged data.
7. The uncorrected attenuation of the water is the gain corrected slab data: $\mu l_w(d)=W_a(d)$.
8. Correct the gain corrected data for beam hardening:

$$\mu l_w^b(d) = \Sigma_{all\ BHC} b_i (\mu l_w(d))^i$$

9. Correct the water attenuation using the initial slab-based correction coefficients:

$$\mu l_w^c(d) = \sum_{all\ coeff.} C_i (\mu l_w^b(d))^i$$

In the aforementioned "attenuation data correction mode" (see Section 2.3 above), the post-processing step is accomplished by the scanner. The corrected attenuation data is simply extracted from the scanner. Once the attenuation data of the acquired water phantoms is generated, they are stored.

Figure 20:
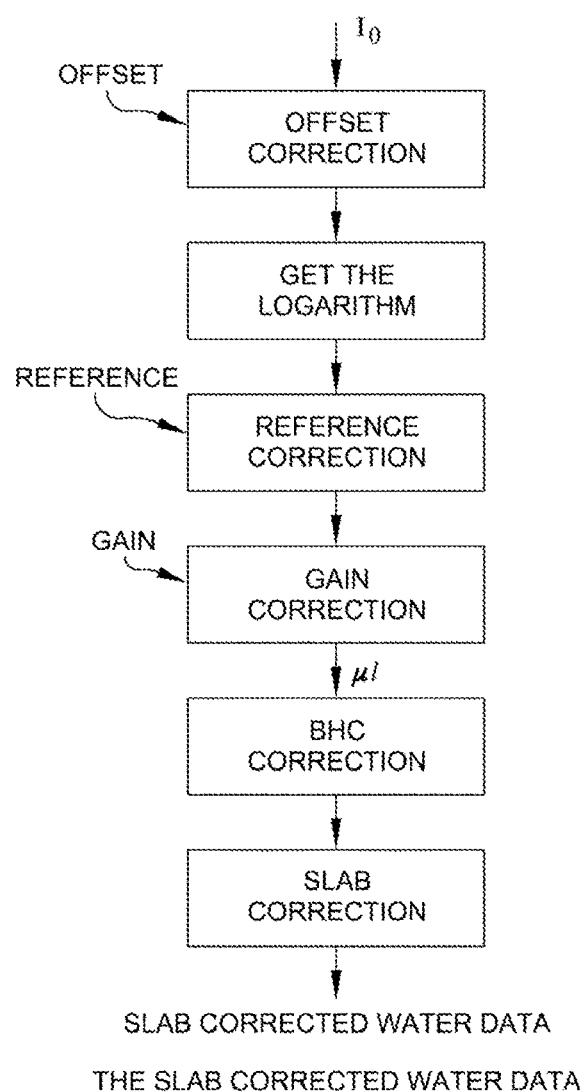
FIG. 20 shows the block diagram of the slab corrected water data.

The next step is to generate a set of ideal attenuation. The corrected attenuation and the ideal attenuation are compared. FIG. 20 shows the block diagram of the slab corrected water data.

2.5 Generating the Ideal Water Data

The ideal water data is generated using the acquired water phantom data. The basic idea is to replace the "raw" water data with "ideal" data and generate the ideal data for each detector. The efficiency of the adjustment depends on the original correction coefficients and the location of the water phantom. Prior methods require knowledge of the exact location of the water phantom relative to the detector. With the novel detector calibration process of the present invention, generating the ideal water data does not require a prior knowledge of the position of the water phantom relative to the detector. Generating the ideal water data of a given detector is described below:

1. Generate full field of view images of the water phantoms using the post-processed data.
2. Automatically locate the water phantom in the scan field of view.
3. Replace only the water inside the image using the ideal CT value of water.
4. Adjust the value of the image background.
5. Recreate the ideal attenuation data by re-projecting the ideal images using the exact model of the scanner.
6. Repeat for all acquired data.

Figure 21:
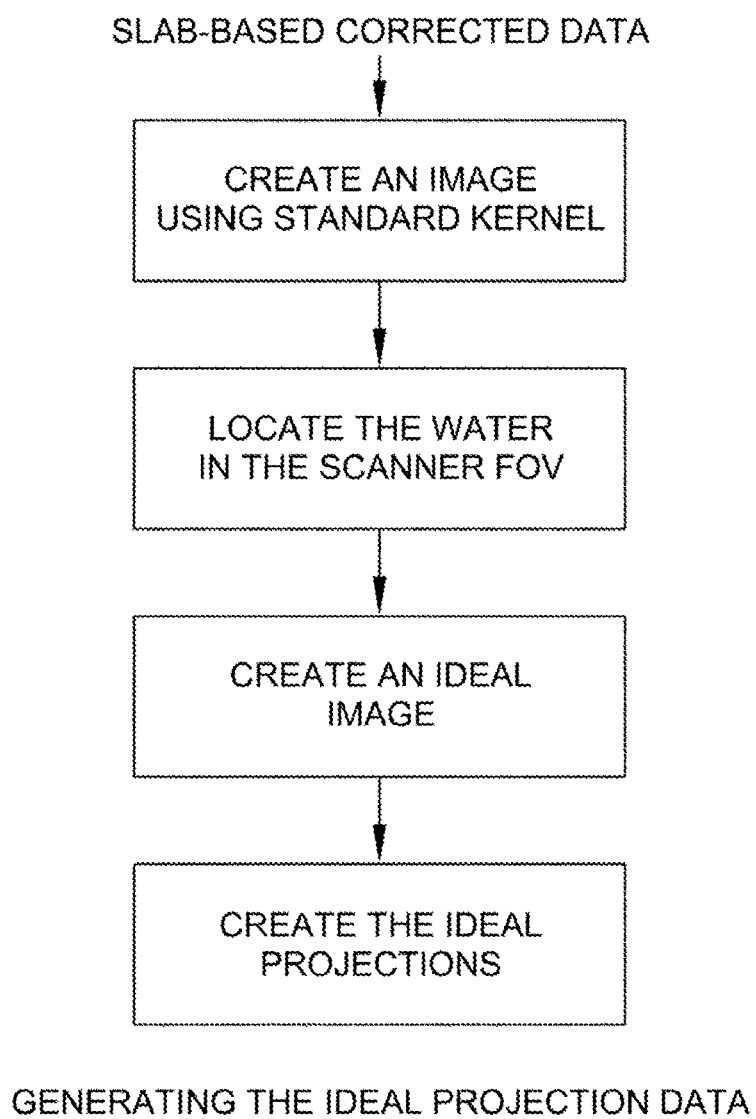
FIG. 21 shows the block diagram of the process of generating the ideal water data.
Figure 22:
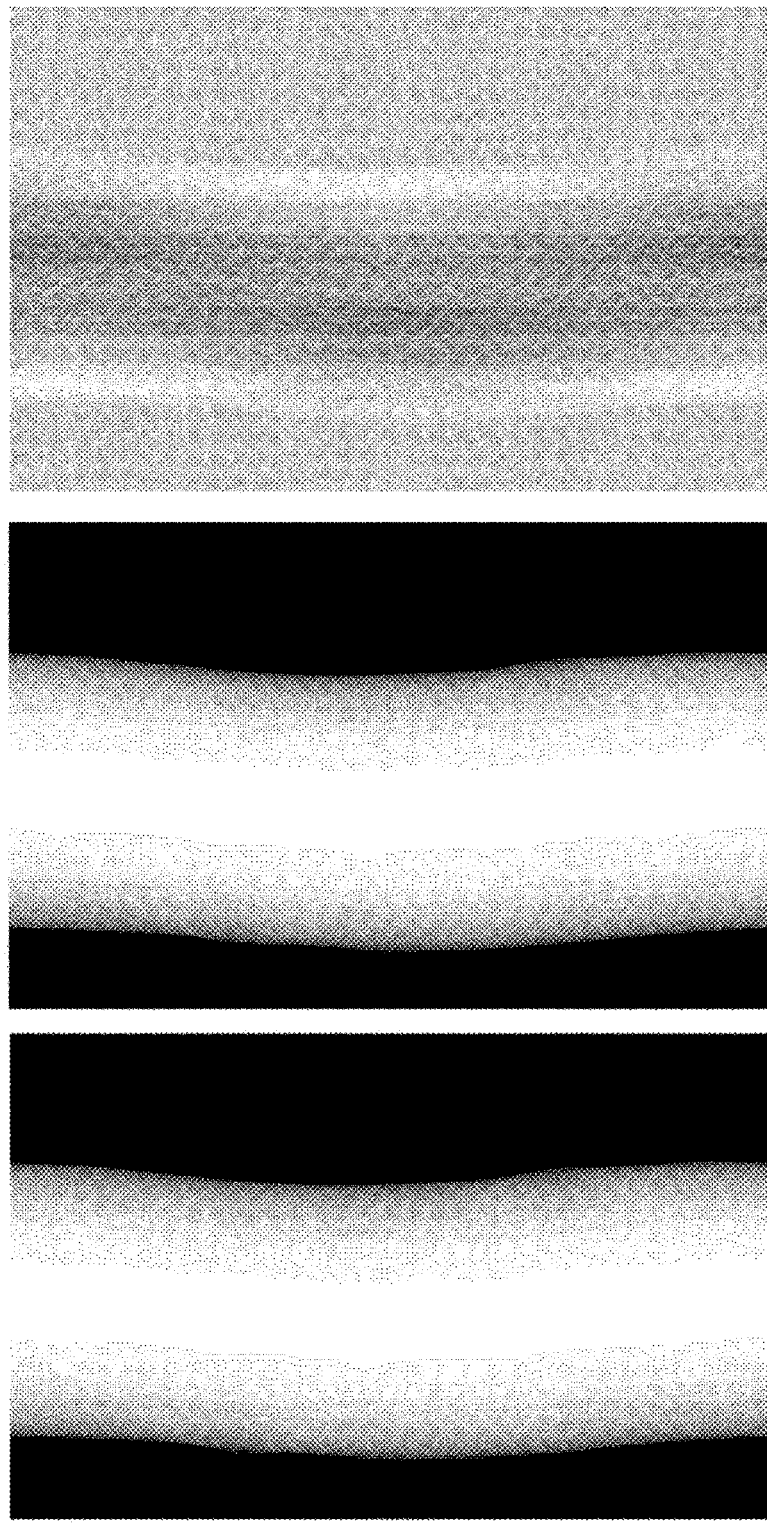
FIG. 22 shows the original and ideal attenuation data.

FIG. 21 shows the block diagram of the process of generating the ideal water data. FIG. 22 shows the original and ideal attenuation data.

2.6 Extracting the Measured Data and the Ideal Data of a Given Detector

Figure 23:
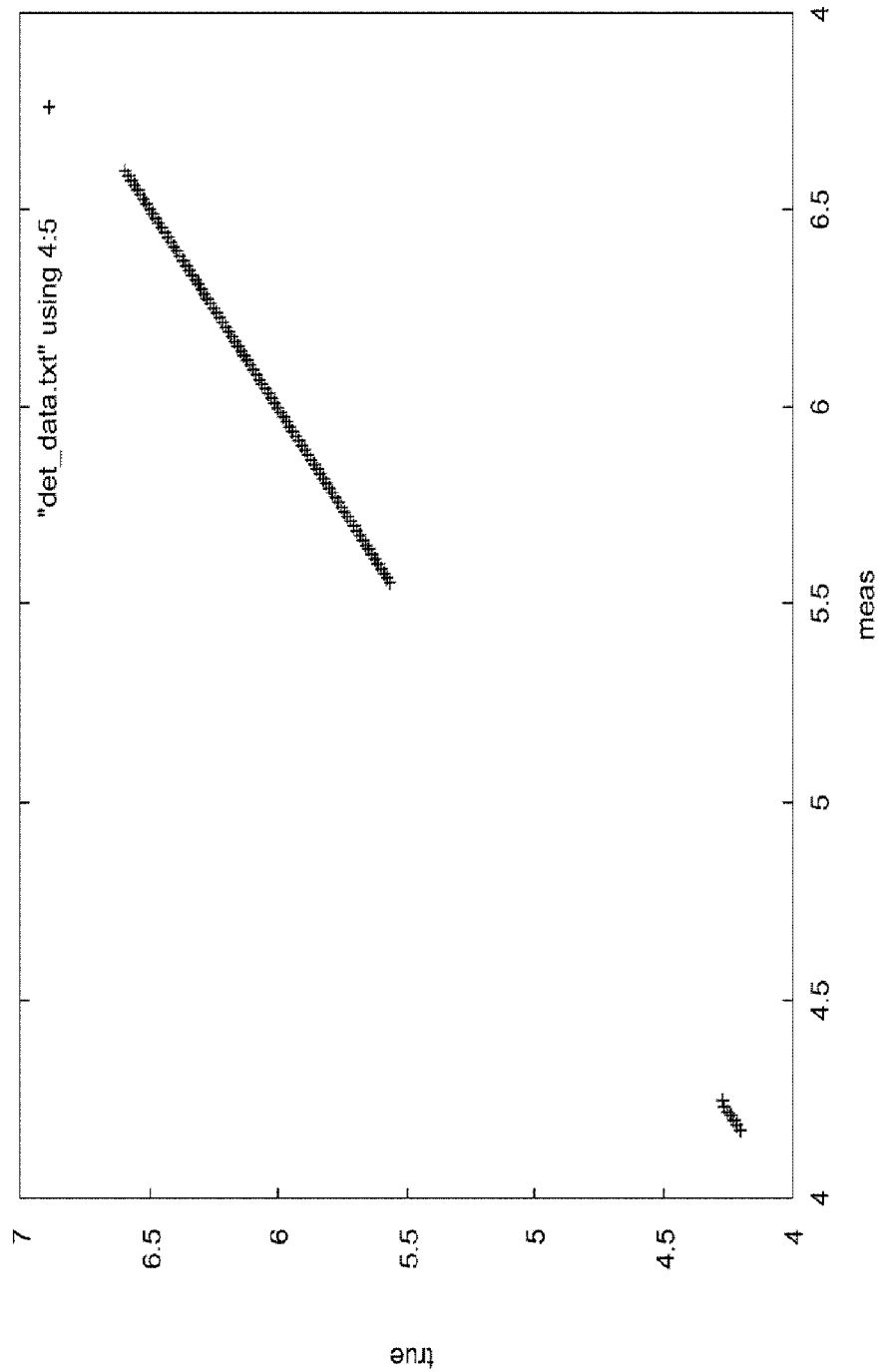
FIG. 23 shows the measured versus the ideal data of a given detector using several water data.

The measured data and the ideal data are extracted for each detector. The data is extracted from each water phantom used in the acquisition. FIG. 23 shows the measured versus the ideal data of a given detector using several water data.

2.7 Computing the Adjustment Coefficient

Figure 24:
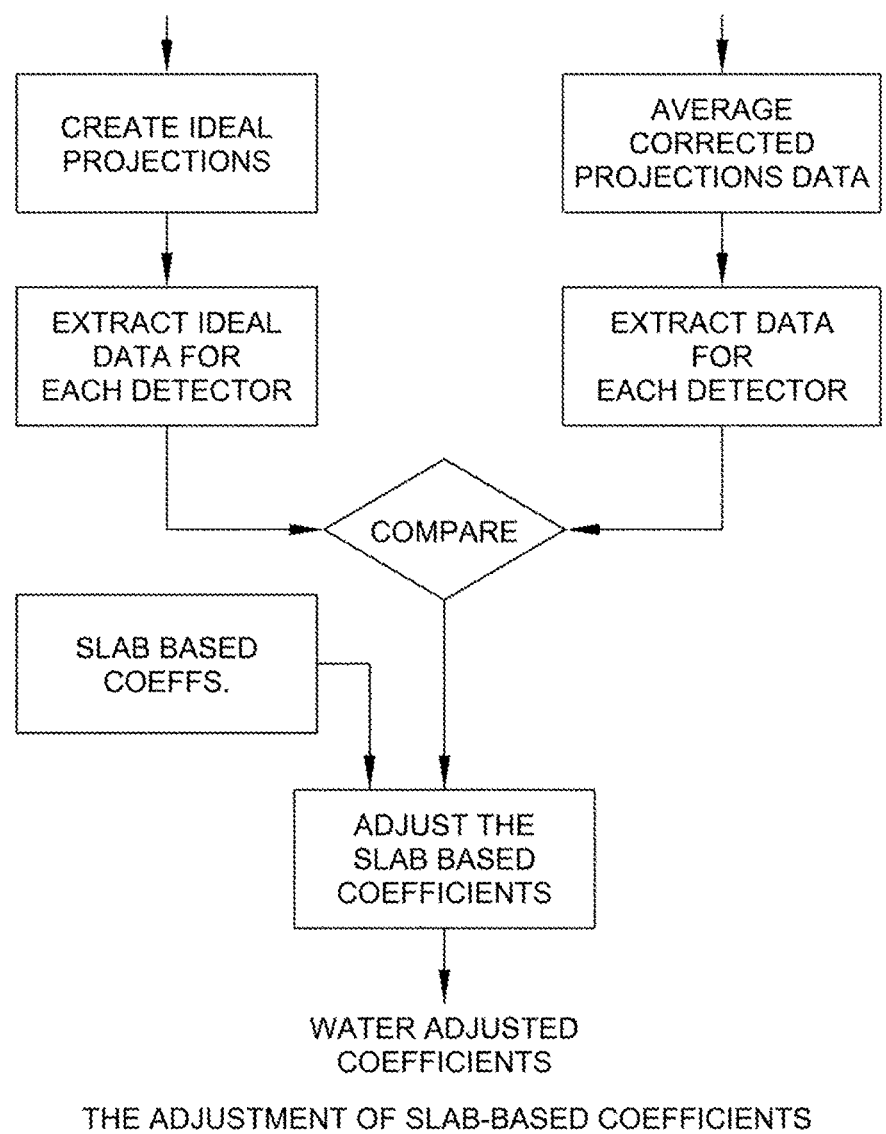
FIG. 24 shows the process of adjusting the slab-based correction coefficients using the water data.

Using the extracted data of each detector, a set of adjustment coefficients are generated using polynomial fitting. Several methods can be used to generate the correction coefficients. One method of generating the correction coefficients uses the Minimum Mean Square Estimate (MMSE). FIG. 24 shows the process of adjusting the slab-based correction coefficients using the water data.

2.8 Adjusting the Slab-Based Correction Coefficients

Figure 25:
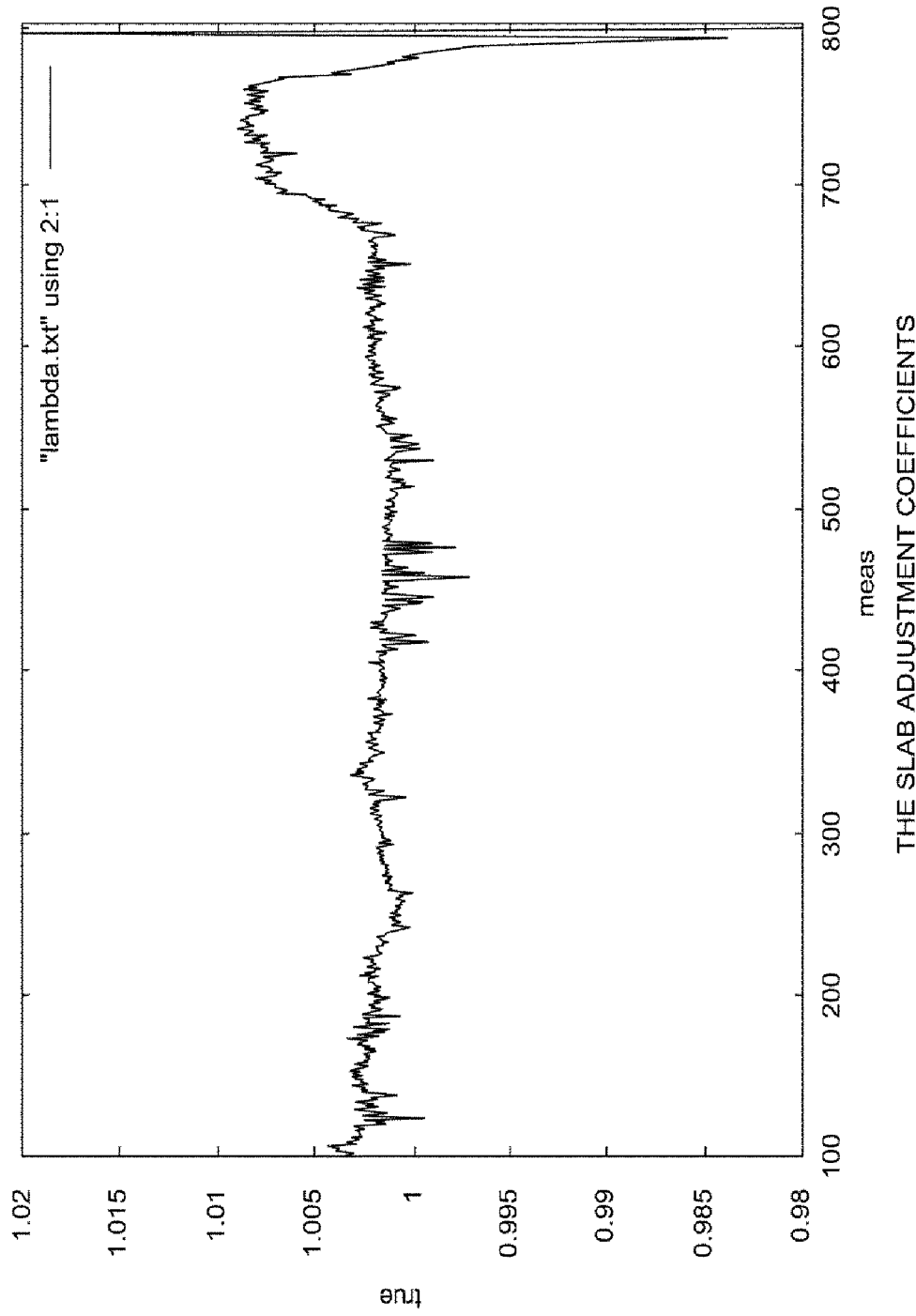
FIG. 25 shows the adjustment coefficients.

The water-based adjustment coefficients generated earlier are used to adjust the slab-based correction coefficient. The step can be omitted here and applied later during the data correction step. FIG. 25 shows the adjustment coefficients.

Application to Other Types of Scanning Systems

It should be appreciated that the present invention is not limited to use in medical applications. Thus, for example, the present invention may be used in connection with CT machines used for non-medical applications, e.g., with CT machines used to scan inanimate objects.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A method for calibrating detectors in a CT scanner, the method comprising:
providing a slab phantom having a known slab phantom scan profile;
scanning the slab phantom with a CT scanner so as to generate a measured slab phantom scan profile;
comparing the known slab phantom scan profile to the measured slab phantom scan profile so as to generate a first scan correction factor;
providing a water phantom having a known water phantom scan profile;
scanning the water phantom with the CT scanner so as to generate a measured water phantom scan profile;
applying the first scan correction factor to the measured water phantom scan profile so as to generate a corrected measured water phantom scan profile;
comparing the known water phantom scan profile to the corrected measured water phantom scan profile so as to generate a second scan correction factor; and
calibrating the detector of the CT scanner using the second scan correction factor.

2. The method according to claim 1, wherein a plurality of slab phantoms are provided, wherein each of the plurality of slab phantoms comprises a known slab phantom scan profile, wherein the plurality of slab phantoms are scanned so as to generate a measured slab phantom scan profile for each of the plurality of slab phantoms, wherein the known slab phantom scan profile is compared to the measured slab phantom scan profile for each of the plurality of slab phantoms so as to generate a plurality of slab phantom correction factors, and further wherein the first scan correction factor is generated based on the plurality of slab phantom correction factors.

3. The method according to claim 1, wherein the water phantom is positioned between an X-ray source and the detector to be calibrated when the water phantom is scanned with the CT scanner, and further wherein X-ray beams are passed through the water phantoms.

4. The method according to claim 1, wherein a plurality of water phantoms are scanned, wherein the measured water phantom scan profile data from the plurality of water phantoms are averaged to generate a composite measured water phantom scan profile, and further wherein the composite measured water phantom scan profile is compared against a known water phantom scan profile so as to generate water-based correction coefficients.

5. The method according to claim 2, wherein the first scan correction factor comprises a polynomial correction function, and further wherein the polynomial correction function is used to generate an initial set of calibration tables.

6. The method according to claim 2, wherein the plurality of slab phantoms are positioned between an X-ray source and the detectors to be calibrated, and wherein X-ray beams are passed through the plurality of slab phantoms.

7. The method according to claim 5, wherein the second scan correction factor is used to adjust coefficients of the polynomial correction function.

8. A method according to claim 6, wherein the plurality of slab phantoms comprises slabs made of a same material.

9. The method according to claim 6, wherein the plurality of slab phantoms are made from acrylic.

10. The method according to claim 6, wherein the plurality of slab phantoms are made from plastic.

11. The method according to claim 6, wherein the plurality of slab phantoms comprise a thin piece of metal on one side of the slab.

12. The method according to claim 6, wherein the measured slab phantom scan profiles for each of the plurality of slab phantoms are averaged so as to generate a composite measured slab phantom scan profile for the plurality of slab phantoms, and further wherein the composite measured slab phantom scan profile is compared against the known slab phantom scan profiles for the plurality of slab phantoms so as to generate the first scan correction factor.

13. The method according to claim 11, wherein the thin piece of metal comprises one from a group consisting of copper and aluminum.

14. The method according to claim 12, wherein the first scan correction factor comprises coefficients that are obtained using a second degree polynomial fit.

15. The method according to claim 3, wherein the water phantom comprises a plurality of water cylinders.

16. The method according to claim 3, wherein a plurality of water phantoms are provided, and further wherein the water phantoms are positioned such that one water phantom is disposed in a center of the detector to be calibrated, and wherein at least one additional water phantom is disposed off-center of the detector to be calibrated.

17. The method according to claim 15, wherein the plurality of water cylinders are interlocked.

* * * * *